US012011338B2

(12) United States Patent
Boltanski

(10) Patent No.: US 12,011,338 B2
(45) Date of Patent: Jun. 18, 2024

(54) MOUNTING SYSTEM FOR OPTICAL ELEMENT OF INTRAORAL SCANNER

(71) Applicant: Align Technology, Inc., San Jose, CA (US)

(72) Inventor: Rami Boltanski, Kiryat Ono (IL)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 18/076,269

(22) Filed: Dec. 6, 2022

(65) Prior Publication Data

US 2023/0210641 A1 Jul. 6, 2023

Related U.S. Application Data

(63) Continuation of application No. 16/996,791, filed on Aug. 18, 2020, now Pat. No. 11,523,885, which is a (Continued)

(51) Int. Cl.

*A61C 9/00* (2006.01)
*A61B 1/00* (2006.01)

(Continued)

(52) U.S. Cl.

CPC ........ *A61C 9/0053* (2013.01); *A61B 1/00096* (2013.01); *A61B 1/00172* (2013.01); *A61B 1/00186* (2013.01); *A61B 1/128* (2013.01); *A61B 1/247* (2013.01); *A61B 5/0062* (2013.01); *A61B 5/0068* (2013.01); *A61B 5/0088* (2013.01); *A61B 5/4547* (2013.01); *G01B 11/24* (2013.01); *G02B 3/0006* (2013.01); *G02B 7/003* (2013.01); *G02B 7/008* (2013.01); *G02B 23/2492* (2013.01); *G02B 26/10* (2013.01); *G02B 27/10* (2013.01); *G02B 27/123* (2013.01); *H05K 1/0201* (2013.01); *H05K 1/181* (2013.01); *H05K 5/0217* (2013.01); *H05K 5/04* (2013.01); *A61B 2562/0233* (2013.01);

(Continued)

(58) Field of Classification Search

CPC ... A61C 9/0053; A61C 13/34; A61B 1/00096; A61B 1/00172; A61B 1/00186; A61B 1/128; A61B 1/247; A61B 5/0062; A61B 5/0068; A61B 5/0088; A61B 5/4547; A61B 2562/0233; G01B 11/24; G02B 3/0006; G02B 7/003; G02B 7/008; G02B 23/2492; G02B 26/10; G02B 27/10; G02B 27/123; H05K 1/0201; H05K 1/181; H05K 5/0217; H05K 5/04; H05K 2201/068; H05K 2201/10151

See application file for complete search history.

(56) References Cited

U.S. PATENT DOCUMENTS 6,099,314 A 8/2000 Kopelman et al.
6,334,772 B1 1/2002 Taub et al.

(Continued)

*Primary Examiner* — Tony Ko

(74) *Attorney, Agent, or Firm* — LOWENSTEIN SANDLER LLP

(57) ABSTRACT

A scanner for scanning a dental site comprises a base, a detector mounted to the base, and an optical element to redirect light reflected off of the dental site towards the detector along a detection axis in a first direction. Two or more flexures couple the optical element to the base, wherein the two or more flexures maintain an alignment of the optical element to the detector with changes in temperature.

20 Claims, 7 Drawing Sheets

100, 130B, 130A, 139A, 139B, 130C, 129B, 112, 129A, 191, 194, 110, 130D, 120, 139C, 139D, 122, 193, 125, 124, 192, 129D, 126

Related U.S. Application Data continuation of application No. 16/052,481, filed on Aug. 1, 2018, now Pat. No. 10,779,914, which is a continuation of application No. 15/287,641, filed on Oct. 6, 2016, now Pat. No. 10,105,199, which is a continuation of application No. 14/316,698, filed on Jun. 26, 2014, now Pat. No. 9,491,863.

(51) Int. Cl.

| | |
|---|---|
| ***A61B 1/12*** | (2006.01) |
| ***A61B 1/247*** | (2006.01) |
| ***A61B 5/00*** | (2006.01) |
| ***G01B 11/24*** | (2006.01) |
| ***G02B 3/00*** | (2006.01) |
| ***G02B 7/00*** | (2021.01) |
| ***G02B 23/24*** | (2006.01) |
| ***G02B 26/10*** | (2006.01) |
| ***G02B 27/10*** | (2006.01) |
| ***G02B 27/12*** | (2006.01) |
| ***H05K 1/02*** | (2006.01) |
| ***H05K 1/18*** | (2006.01) |
| ***H05K 5/02*** | (2006.01) |
| ***H05K 5/04*** | (2006.01) |
| *A61C 13/34* | (2006.01) |

(52) U.S. Cl.

CPC ........ *A61C 13/34* (2013.01); *H05K 2201/068* (2013.01); *H05K 2201/10151* (2013.01)

(56) References Cited

U.S. PATENT DOCUMENTS

| | | | |
|---|---|---|---|
| 6,334,853 | B1 | 1/2002 | Kopelman et al. |
| 6,463,344 | B1 | 10/2002 | Pavlovskaia et al. |
| 6,542,249 | B1 | 4/2003 | Kofman et al. |
| 6,633,789 | B1 | 10/2003 | Nikolskiy et al. |
| 6,664,986 | B1 | 12/2003 | Kopelman et al. |
| 6,697,164 | B1 | 2/2004 | Babayoff et al. |
| 6,845,175 | B2 | 1/2005 | Kopelman et al. |
| 6,979,196 | B2 | 12/2005 | Nikolskiy et al. |
| 7,030,383 | B2 | 4/2006 | Babayoff et al. |
| 7,202,466 | B2 | 4/2007 | Babayoff et al. |
| 7,255,558 | B2 | 8/2007 | Babayoff et al. |
| 7,286,954 | B2 | 10/2007 | Kopelman et al. |
| 7,373,286 | B2 | 5/2008 | Nikolskiy et al. |
| 7,507,088 | B2 | 3/2009 | Taub et al. |
| 7,545,372 | B2 | 6/2009 | Kopelman et al. |
| 7,916,911 | B2 | 3/2011 | Kaza et al. |
| 8,108,189 | B2 | 1/2012 | Chelnokov et al. |
| 8,244,028 | B2 | 8/2012 | Kuo et al. |
| 8,587,582 | B2 | 11/2013 | Matov et al. |
| 8,948,482 | B2 | 2/2015 | Levin |
| D742,518 | S | 11/2015 | Barak et al. |
| 9,192,305 | B2 | 11/2015 | Levin |
| 9,261,356 | B2 | 2/2016 | Lampert et al. |
| 9,261,358 | B2 | 2/2016 | Atiya et al. |
| 9,299,192 | B2 | 3/2016 | Kopelman |
| D760,901 | S | 7/2016 | Barak et al. |
| 9,393,087 | B2 | 7/2016 | Moalem |
| 9,408,679 | B2 | 8/2016 | Kopelman |
| 9,431,887 | B2 | 8/2016 | Boltanski |
| 9,439,568 | B2 | 9/2016 | Atiya et al. |
| 9,451,873 | B1 | 9/2016 | Kopelman et al. |
| D768,861 | S | 10/2016 | Barak et al. |
| D771,817 | S | 11/2016 | Barak et al. |
| D774,193 | S | 12/2016 | Makmel et al. |
| 9,510,757 | B2 | 12/2016 | Kopelman et al. |
| 9,660,418 | B2 | 5/2017 | Atiya et al. |
| 9,668,829 | B2 | 6/2017 | Kopelman |
| 9,675,430 | B2 | 6/2017 | Verker et al. |
| 9,693,839 | B2 | 7/2017 | Atiya et al. |
| 9,717,402 | B2 | 8/2017 | Lampert et al. |
| 9,724,177 | B2 | 8/2017 | Levin |
| 9,844,426 | B2 | 12/2017 | Atiya et al. |
| 10,076,389 | B2 | 9/2018 | Wu et al. |
| 10,098,714 | B2 | 10/2018 | Kuo |
| 10,108,269 | B2 | 10/2018 | Sabina et al. |
| 10,111,581 | B2 | 10/2018 | Makmel |
| 10,111,714 | B2 | 10/2018 | Kopelman et al. |
| 10,123,706 | B2 | 11/2018 | Elbaz et al. |
| 10,136,972 | B2 | 11/2018 | Sabina et al. |
| 10,380,212 | B2 | 8/2019 | Elbaz et al. |
| 10,390,913 | B2 | 8/2019 | Sabina et al. |
| 10,453,269 | B2 | 10/2019 | Furst |
| 10,456,043 | B2 | 10/2019 | Atiya et al. |
| 10,499,793 | B2 | 12/2019 | Ozerov et al. |
| 10,504,386 | B2 | 12/2019 | Levin et al. |
| 10,507,087 | B2 | 12/2019 | Elbaz et al. |
| 10,517,482 | B2 | 12/2019 | Sato et al. |
| 10,695,150 | B2 | 6/2020 | Kopelman et al. |
| 10,708,574 | B2 | 7/2020 | Furst et al. |
| 10,772,506 | B2 | 9/2020 | Atiya et al. |
| 10,813,727 | B2 | 10/2020 | Sabina et al. |
| 10,888,399 | B2 | 1/2021 | Kopelman et al. |
| 10,952,816 | B2 | 3/2021 | Kopelman |
| 10,980,613 | B2 | 4/2021 | Shanjani et al. |
| 11,013,581 | B2 | 5/2021 | Sabina et al. |
| D925,739 | S | 7/2021 | Shalev et al. |
| 11,096,765 | B2 | 8/2021 | Atiya et al. |
| 11,238,586 | B2 | 2/2022 | Minchenkov et al. |
| 11,367,192 | B2 | 6/2022 | Kopelman et al. |
| 11,455,727 | B2 | 9/2022 | Minchenkov et al. |
| 11,478,132 | B2 | 10/2022 | Kopelman et al. |
| 11,563,929 | B2 | 1/2023 | Saphier et al. |
| 2009/0279103 | A1* | 11/2009 | Thiel .................... A61B 5/0068 433/31 |
| 2015/0029309 | A1* | 1/2015 | Michaeli ................ G01B 11/25 348/46 |
| 2019/0029784 | A1 | 1/2019 | Moalem et al. |
| 2019/0388193 | A1 | 12/2019 | Saphier et al. |
| 2020/0281702 | A1 | 9/2020 | Kopelman et al. |
| 2021/0030503 | A1 | 2/2021 | Shalev et al. |
| 2021/0059796 | A1 | 3/2021 | Weiss et al. |
| 2021/0068773 | A1 | 3/2021 | Moshe et al. |
| 2021/0121049 | A1 | 4/2021 | Rudnitsky et al. |
| 2021/0128281 | A1 | 5/2021 | Peleg |
| 2021/0137653 | A1 | 5/2021 | Saphier et al. |
| 2021/0196152 | A1 | 7/2021 | Saphier et al. |

* cited by examiner

MOUNTING SYSTEM FOR OPTICAL ELEMENT OF INTRAORAL SCANNER

RELATED APPLICATIONS

The present application is a continuation of U.S. patent application Ser. No. 16/996,791, filed Aug. 18, 2020, which is a continuation of U.S. patent application Ser. No. 16/052,481, filed Aug. 1, 2018, issued as U.S. Pat. No. 10,779,914 on Sep. 22, 2020, which is a continuation of U.S. patent application Ser. No. 15/287,641, filed Oct. 6, 2016, issued as U.S. Pat. No. 10,105,199 on Oct. 23, 2018, which is a continuation application of U.S. patent application Ser. No. 14/316,698, filed Jun. 26, 2014, issued as U.S. Pat. No. 9,491,863 on Nov. 8, 2016, all of which are incorporated by reference herein.

TECHNICAL FIELD

Embodiments of the present invention relate to the field of mounting systems and, in particular, to a system and method for mounting an optical element to a printed circuit board (PCB).

BACKGROUND

In prosthodontic procedures designed to implant a dental prosthesis in the oral cavity, the dental site at which the prosthesis is to be implanted may be measured accurately and studied carefully, so that a prosthesis such as a crown, denture or bridge, for example, can be properly designed and dimensioned to fit in place. A good fit, for example, enables mechanical stresses to be properly transmitted between the prosthesis and the jaw and minimizes infection of the gums via the interface between the prosthesis and the dental site.

Some procedures call for removable prosthetics to be fabricated to replace one or more missing teeth, such as a partial or full denture, in which case the surface contours of the areas where the teeth are missing may be reproduced accurately so that the resulting prosthetic fits over the edentulous region with even pressure on the soft tissues.

In some practices, the dental site is prepared by a dental practitioner, and a positive physical model of the dental site is constructed. Alternatively, the dental site may be scanned to provide three-dimensional (3D) data of the dental site. In either case, the virtual or real model of the dental site may be sent to a dental lab that manufactures the prosthesis based on the model. However, if the model is deficient or undefined in certain areas, or if the preparation was not optimally configured for receiving the prosthesis, the design of the prosthesis may be less than optimal. For example, if the insertion path implied by the preparation for a closely-fitting coping would result in the prosthesis colliding with adjacent teeth, the coping geometry may be altered to avoid the collision. Further, if the area of the preparation containing a finish line lacks definition, it may not be possible to properly determine the finish line and thus the lower edge of the coping may not be properly designed. Indeed, in some circumstances, the model is rejected and the dental practitioner then re-scans the dental site, or reworks the preparation, so that a suitable prosthesis may be produced.

In orthodontic procedures, it can be important to provide a model of one or both jaws. Where such orthodontic procedures are designed virtually, a virtual model of the oral cavity is also beneficial. Such a virtual model may be obtained by scanning the oral cavity directly, or by producing a physical model of the dentition, and then scanning the model with a suitable scanner.

Thus, in both prosthodontic and orthodontic procedures, obtaining a 3D model of a dental site in the oral cavity may be an initial procedure that is performed. When the 3D model is a virtual model, the more complete and accurate the scans of the dental site are, the higher the quality of the virtual model, and thus the greater the ability to design an optimal prosthesis or orthodontic treatment appliance.

BRIEF DESCRIPTION OF THE DRAWINGS

The present invention is illustrated by way of example, and not by way of limitation, in the figures of the accompanying drawings.

DETAILED DESCRIPTION

A mounting system is described herein including a base and a number of flexures attached to the base. The base may define a base plane perpendicular to a z-axis and the flexures may be pieces of material that protrude from the base in the direction of the z-axis and that are substantially flat in a direction of a corresponding y-axis radiating from the z-axis.

A mounted element may be mounted to the base by attaching the flexures to the mounted element. The flexures may be arranged such that thermal expansion or contraction of the mounted element and/or the base bends the flexures outwards or inwards, e.g., in the direction of a corresponding y-axis, without bending the flexures in any other direction, e.g., in a direction perpendicular to the y-axis and the z-axis. Thus, the flexures allow for thermal expansion or contraction of the mounted element with minimal stress on components of the mounting system, yet prevent translational or rotational movement of the mounted element with respect to the base.

Figure 1:
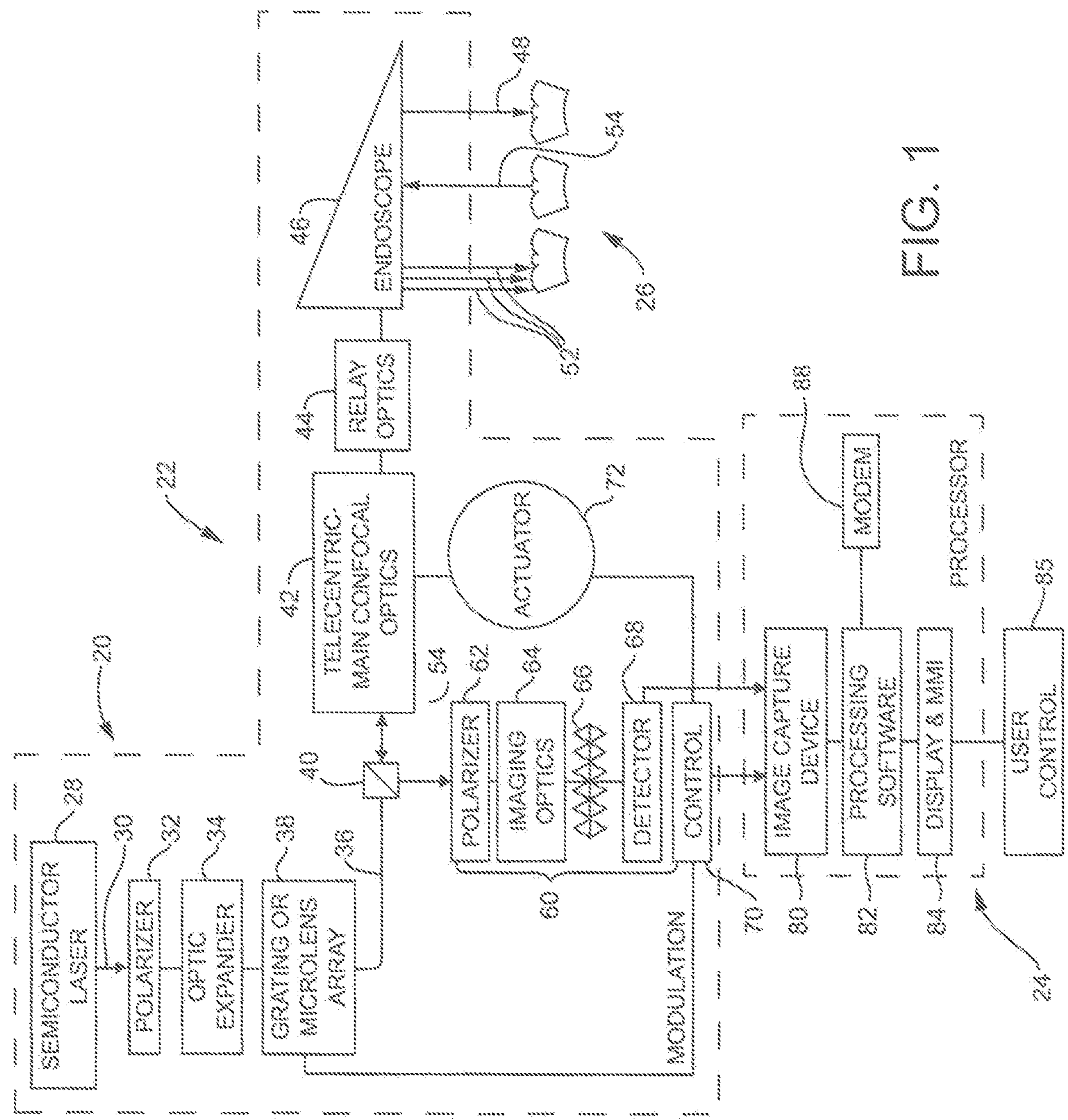
FIG. 1 illustrates a functional block diagram of an optical device according to one embodiment.

FIG. 1 illustrates a functional block diagram of an optical device 22 according to one embodiment. The optical device 22 may be a scanner, such as an intraoral scanner. The optical device 22 includes a light source to generate light, such as a semiconductor laser 28 that emits a laser light (represented by the arrow 30). The light passes through a polarizer 32 which gives rise to a certain polarization of the light passing through polarizer 32. The light then enters into an optic expander 34 which improves the numerical aperture of the light beam 30. The light then passes through a module 38 (e.g., a grating or a microlens array) that splits the parent beam 30 into multiple incident light beams 36, represented in FIG. 1 by a single line for ease of illustration. For example, the module 38 may split the parent beam 30 into a two-dimensional array of light beams.

The optical device 22 further includes a beam splitter 40 that allows transfer of light from the laser source through the downstream optics, but redirects light travelling in the opposite direction. Thus, the beam splitter 40 may transmit a two-dimensional array of light beams from the module 38 to a target (via the downstream optics), but redirect a reflected two-dimensional array of light beams from the target to a detector (as described below). In other embodiments, rather than a beam splitter, other optical components with a similar function may also be used, e.g. partially transparent mirror having a small central aperture. The aperture in the mirror improves the measurement accuracy of the apparatus.

The optical device 22 further includes confocal optics 42 operating in a telecentric mode, relay optics 44, and an endoscope 46. In one embodiment, telecentric confocal optics avoid distance-introduced magnification changes and maintain the same magnification of the image over a wide range of distances in the Z direction (the Z direction being the direction of beam propagation, also referred to as the Z axis or lens axis). The relay optics 44 allow maintenance of a certain numerical aperture of the beam's propagation.

The endoscope 46 typically includes a rigid, light-transmitting medium. The rigid, light-transmitting medium may be a hollow object defining within it a light transmission path or an object made of a light transmitting material (e.g., a glass body or tube). At its end, the endoscope typically includes a mirror of the kind ensuring a total internal reflection. The mirror may direct incident light beams towards a teeth segment 26 that is being scanned. The endoscope 46 thus emits multiple incident light beams 48 impinging on to the surface of the teeth segment 26.

The incident light beams 48 form an array of light beams arranged in an X-Y plane propagating along the Z-axis. If the surface on which the incident light beams hit is an uneven surface, illuminated spots 52 are displaced from one another along the Z-axis, at different (Xi, Yi) locations. Thus, while a spot at one location may be in focus of the optical element 42, spots at other locations may be out-of-focus. Therefore, the light intensity of the returned light beams (see below) of the focused spots will be at its peak, while the light intensity at other spots will be off peak. Thus, for each illuminated spot, multiple measurements of light intensity are made at different positions along the Z-axis. For each of such (Xi, Yi) location, typically the derivative of the intensity over distance (Z) will be made, the $Z_i$, yielding maximum derivative, $Z_0$, will be the in-focus distance. As pointed out above, where, as a result of use of the partially transparent mirror 40, the incident light forms a light disk on the surface when out of focus and a complete light spot only when in focus, the distance derivative will be larger when approaching in-focus position thus increasing accuracy of the measurement.

The light scattered from each of the light spots includes a beam travelling initially in the Z-axis along the opposite direction of the optical path traveled by the incident light beams. Each returned light beam 54 corresponds to one of the incident light beams 36. Given the unsymmetrical properties of the beam splitter 40, the returned light beams are reflected in the direction of the detection optics 60. The detection optics 60 include a polarizer 62 that has a plane of preferred polarization oriented normal to the plane polarization of polarizer 32. The returned polarized light beam 54 pass through an imaging optic 64, typically one or more lenses, and then through a matrix 66 including an array of pinholes. A detector 68, such as a CCD (charge-coupled device) camera, has a matrix of sensing elements each representing a pixel of the image and each one corresponding to one pinhole in the array 66. Thus, the detector 68 may include a two-dimensional array of sensors, where each sensor determines an intensity of light impinging on the sensor.

The detector 68 is connected to the image-capturing module 80 of processor unit 24. Thus, each light intensity measured in each of the sensing elements of the detector 68 is received and analyzed by a processor 24.

The optical device 22 further includes a control module 70 connected to a controlling operation of both the semiconductor laser 28 and an actuator 72. The actuator 72 is linked to the telecentric confocal optics 42 to change the relative location of the focal plane of the confocal optics 42 along the Z-axis. In a single sequence of operation, the control unit 70 induces the actuator 72 to displace the confocal optics 42 to change the focal plane location and then, after receipt of a feedback that the location has changed, the control module 70 will induce the laser 28 to generate a light pulse. At the same time, the control module 70 will synchronize the image capturing module 80 to grab data representative of the light intensity from each of the sensing elements of the detector 68. Then, in subsequent sequences the focal plane will change in the same manner and the data capturing will continue over a wide focal range.

The image capturing device 80 is connected to processing software 82 which then determines the relative intensity in each pixel over the entire range of focal planes of optics 42, 44. As explained above, once a certain light spot is in focus, the measured intensity will be maximal. Thus, by determining the $Z_i$, corresponding to the maximal light intensity or by determining the maximum displacement derivative of the light intensity, for each pixel, the relative position of each light spot along the Z-axis can be determined. Thus, data representative of the three-dimensional pattern of a surface in the teeth segment can be obtained. This three-dimensional representation may be displayed on a display 84 and manipulated for viewing, e.g. viewing from different angles, zooming-in or out, by a user control module 86 (e.g., a computer keyboard, touchpad, mouse, etc.). In addition, the data representative of the surface topology may be transmitted through an appropriate data port, e.g. a modem 88, through any communication network (e.g., a local area network (LAN), wide area network (WAN), public network such as the Internet, etc.) to a recipient.

In embodiments, one or more of the optical elements (e.g., the polarizer 32, optic expander 34, microlens array 38, beam splitter 40, confocal optics 42, detection optics 60, etc.) may be mounted to a base using an arrangement of flexures as described herein below in greater detail. The flexures may secure the optical elements in a manner that allows for thermal expansion or contraction of the optical element and/or base with minimal stress on components of the mounting system, yet prevents translational or rotational movement of the mounted element with respect to the base. Thus, proper alignment of the optical components may be maintained throughout temperature shifts.

Figure 2:
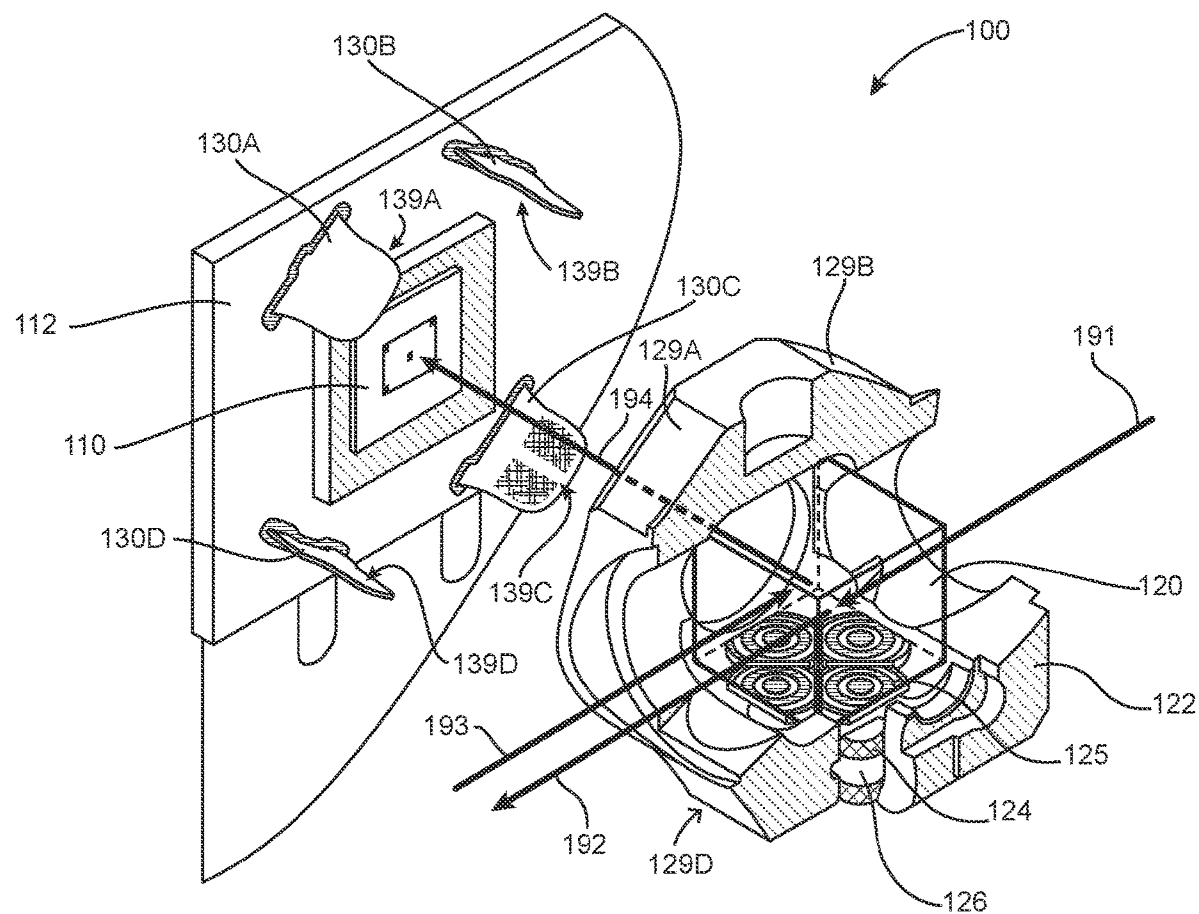
FIG. 2 illustrates an exploded perspective view of an optical system according to one embodiment.

FIG. 2 illustrates an exploded perspective view of an optical system 100 according to one embodiment. The optical system 100 may be included in a scanner, such as an intraoral scanner, which may have additional components such as those described above with respect to FIG. 1. The optical system 100 includes a detector 110 that determines one or more intensities of light impinging on one or more locations of the detector 110. The detector 110 may include a two-dimensional array of sensors, wherein each sensor detects the intensity of light impinging on the sensor. In one embodiment, the detector 110 includes a CCD (charge-coupled device) camera.

The optical system 100 includes an optical element 120 that redirects light towards the detector 120. The optical element 120 allows light from a light source (indicated by arrow 191) to pass through the optical element 120 towards a target (indicated by arrow 192), but redirects light reflected from target (indicated by arrow 193) towards the detector 110 along a detection axis (indicated by arrow 194). The optical element 120 may include, for example, a beam splitter. In another embodiment, the optical element 120 may include a partially transparent mirror. The optical element may include, for example, glass or plastic or any transparent or reflective material.

The optical element 120 may be enclosed by or housed within a housing 122 (shown partially cutaway in FIG. 2). In one embodiment, the housing 122 is metal, e.g. aluminum. The optical element 120 may be coupled to the housing 122 by one or more studs 124. The studs 124 may include a head 125 that attaches to a bottom of the optical element 120 and a root 126 that attaches to the housing 122.

The detector 110 may be mounted to a base 112, such as a printed circuit board (PCB) composed of FR-4, FR-2, BT-Epoxy, Cyanate Ester, Polyimide, Polytetrafluoroethylene (PTFE), or any other material. The base 112 may include conductive traces coupled to a processing device for receiving the intensity data generated by the detector 110. The base 112 defines a base plane substantially perpendicular to the detection axis.

The optical system 100 includes a number of flexures 130A-130D for coupling the optical element 120 to the detector 110. Whereas FIG. 2 shows the optical system 100 with four flexures 130A-130D, the optical system 100 may include more or fewer flexures. For example, in one embodiment, the optical system 100 includes two flexures which may be disposed on opposite sides of the detector 110. In another embodiment, the optical system 100 includes three or more flexures. In one embodiment, the optical system 100 includes eight flexures.

Each of the flexures 130A-130D may be a substantially flat piece of material coupled to and protruding from the base 112. For example, the flexures 130A-130D may be welded or soldered to the base 112. In one embodiment, the flexures 130A-130D are beryllium copper. The flexures 130A-130D may also be composed of other high strength flexible materials, such as other metals. Although the flexures 130A-130D may be substantially flat, an attachment face 139A-139D of each of the flexures 130A-130D may be textured to improve adhesion with the optical element 120 or a corresponding attachment face 129A-129D of the housing 122.

As noted above, FIG. 2 is an exploded view of the optical system 100. Once constructed, the flexures 130A-130D couple the detector 110 to the optical element 120. In one embodiment, construction of the optical system 100 includes aligning the optical element 120 with the detector 110 such that a center of the redirected light 194 (e.g., a center of a two-dimensional array of beams) is redirected to a center of the detector 110. In one embodiment, the flexures 130A-130D are coupled to the optical element 120 by attachment to the housing 122. In one embodiment, the flexures 130A-130D are glued to the housing 122. In one embodiment, glue is applied to the attachment face 139A-139D of the flexure 130A-130D and the attachment face 139A-139D is glued to a corresponding attachment face 129A-129D of the housing 122.

The flexures 130A-130D may be arranged such that thermal expansion or contraction of the optical element 120 (or the housing 122) with respect to the detector 110 bends the flexures outwards or inwards, e.g., in a direction radiating from the detection axis, without substantially bending the flexures in any other direction, e.g., a direction perpendicular to the radiating direction and the detection axis direction. For example, whereas the flexures may bend outward up to a millimeter, bending in other directions may be limited to less than a micron, maintaining sub-micron accuracy of the alignment. Thus, the flexures 130A-130D allow for thermal expansion or contraction of the optical element 120 (or the housing 122) with minimal stress on components of the mounting system 200, yet prevent translational or rotational movement of the optical element 120 with respect to the detector 110. Thermal expansion or contraction may occur due to the optical element 120 (e.g., a beam splitter composed of glass) having a first coefficient of thermal expansion that is different from a second coefficient of thermal expansion of at least one of the detector 110 or the base 112.

Figure 3:
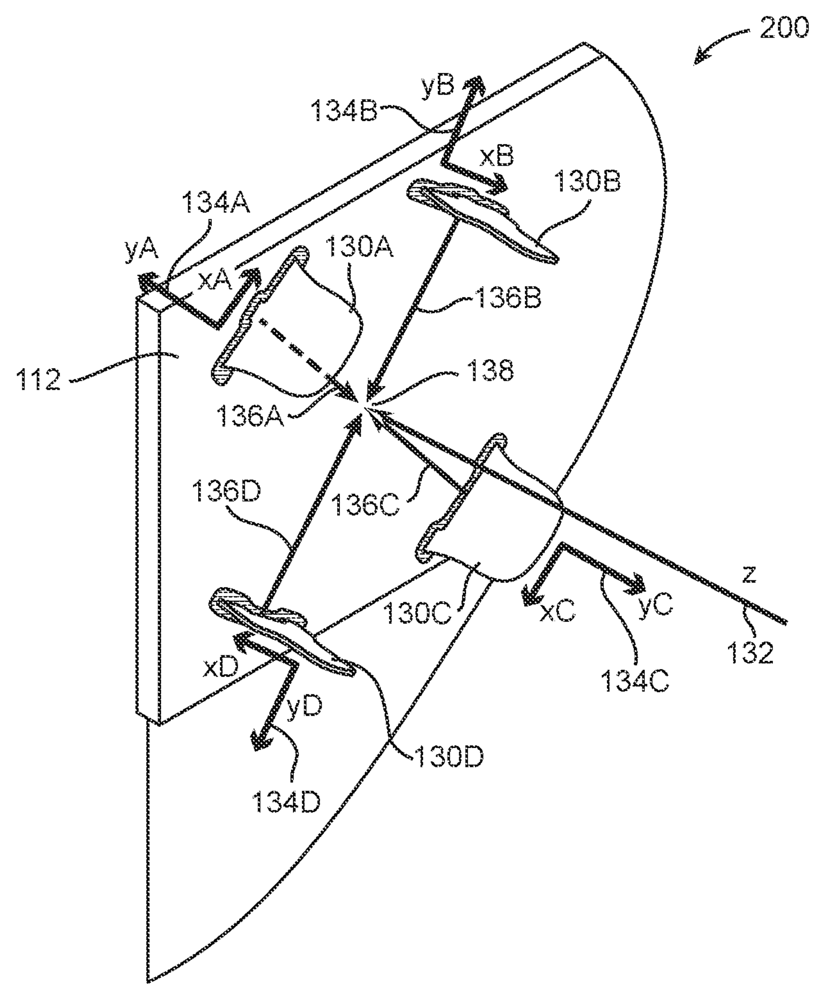
FIG. 3 illustrates a perspective view of a mounting system according to one embodiment.

FIG. 3 illustrates a perspective view of a mounting system 200 according to one embodiment. The mounting system 200 may include the base 112 and flexures 130A-130D of FIG. 2. Although FIG. 3 shows four flexures 130A-130D, the mounting system 200 may include more or fewer flexures. As described above, a detector and an optical element may be coupled together using the mounting system 200. However, the mounting system 200 may be used to couple other components.

The base 112 includes a substantially flat surface defining a base plane perpendicular to a z-axis 132. The flexures 130A-130D are substantially flat pieces of material protruding from the base in the direction of the z-axis 132. The flexures 130A-130D are respectively associated with xy-axes 134A-134D perpendicular to the z-axis, wherein each y-axis is perpendicular to and radiating from the z-axis and wherein each x-axis is perpendicular to both the z-axis and the corresponding x-axis. The xy-axes 134A-134D may be defined by an attachment face spanning a corresponding xz-plane, referred to as a flexure plane, which is perpendicular to the base plane and, thus, parallel to the z-axis. The flexure planes, in turn, define flexure lines 136A-136D normal to the flexure plane (e.g., along the y-axis). The flexure lines 136A-136D meet at an intersection point 138. The flexures 130A-130D may be flexible along a respective flexure line 136A-136D and rigid perpendicular to the respective flexure line 136A-136D.

With respect to FIG. 3, the flexures 130A-130D include a first flexure 130A defining a first flexure line 136A, a second flexure 1308 defining a second flexure line 136A collinear with the first flexure line 136A, a third flexure 130C defining a third flexure line 136C perpendicular to the first flexure line 136A, and a fourth flexure 130D defining a fourth flexure line 136C collinear with the third flexure line 136C. The flexure lines 136A-136D meet at the intersection point 138.

As discussed above, the optical element 120 may be aligned with the detector 110 such that a center of the redirected light 194 (e.g., a center of a two-dimensional array of beams) is redirected to a center of the detector 110. The detector 110 may be mounted on the base such that the flexures surround, but do not contact the detector 110. The intersection point 138 provides a stationary point of the system such that the center of the redirected light 194 is redirected to the center of the detector regardless of thermal expansion or contraction of the components of the system, as the flexures 130A-130D are rigid along a respective first axis and flexible along a respective second axis, the respective first axis and the respective second axis being generally parallel to a face of the detector. Moreover, the optical element 120 may maintain a fixed position, such that each pixel of the detector remain aligned with respective source beams to sub-micron accuracy and stability over a wide range of thermal conditions.

In one embodiment, a mounted element (such as the optical element 120 and housing 122 of FIG. 2) includes substantially flat attachment faces (such as the attachment faces 129A-129D of the housing 122 of FIG. 2) that respectively define face planes, each of the three or more face planes being parallel to one of the flexure planes. Mounting the mounted element may include aligning the mounted element to the detector and attaching the flexures 130A-130D to the mounted element, e.g., by gluing attachment faces of the flexures 130A-130D to attachment faces of the mounted element. The mounted element may be mounted to the base 112 such that a center of the mounted element is aligned with the intersection point 138.

Each flexure 130A-130D may have a height in a first direction (e.g., along the z-axis), a thickness in a second direction (e.g., along the y-axis), and a width in a third direction (e.g., along the x-axis.). In one embodiment, the thickness is substantially smaller than the height and the width. For example, in one embodiment, the thickness is less than one-tenth the height and the width. In one embodiment, the thickness is less than one millimeter and the height and width are at least ten millimeters. In one embodiment, the width is greater than the height. For example, the width may be at least 20% greater than the height. In another embodiment, the width and height are approximately equal.

In one embodiment, the flexures 130A-130D are bent at approximately a 90-degree angle at one end that attaches to the base 112. This may provide a greater surface area to attach the flexures 130A-130D to the base 112. In one embodiment, the bent end of the flexures 130A-130D is divided into multiple sections (e.g., three sections), with a one or more sections being bent 90-degrees in a first direction and one or more other sections being bent at 90 degrees in an opposite direction.

Figure 4A:
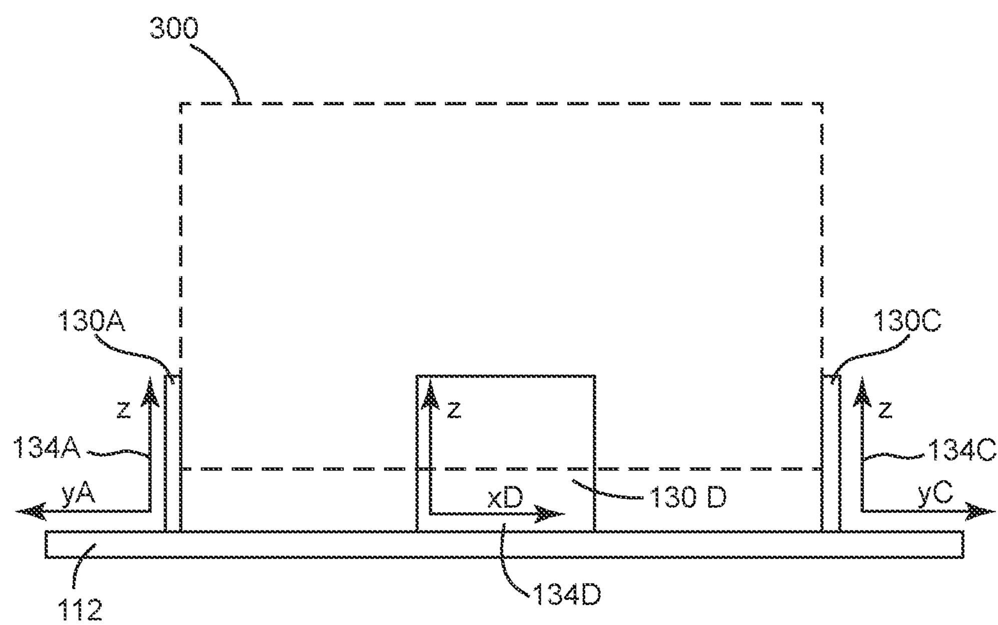
FIG. 4A illustrates a side view of the mounting system of FIG. 3 in a thermally neutral configuration.
Figure 4B:
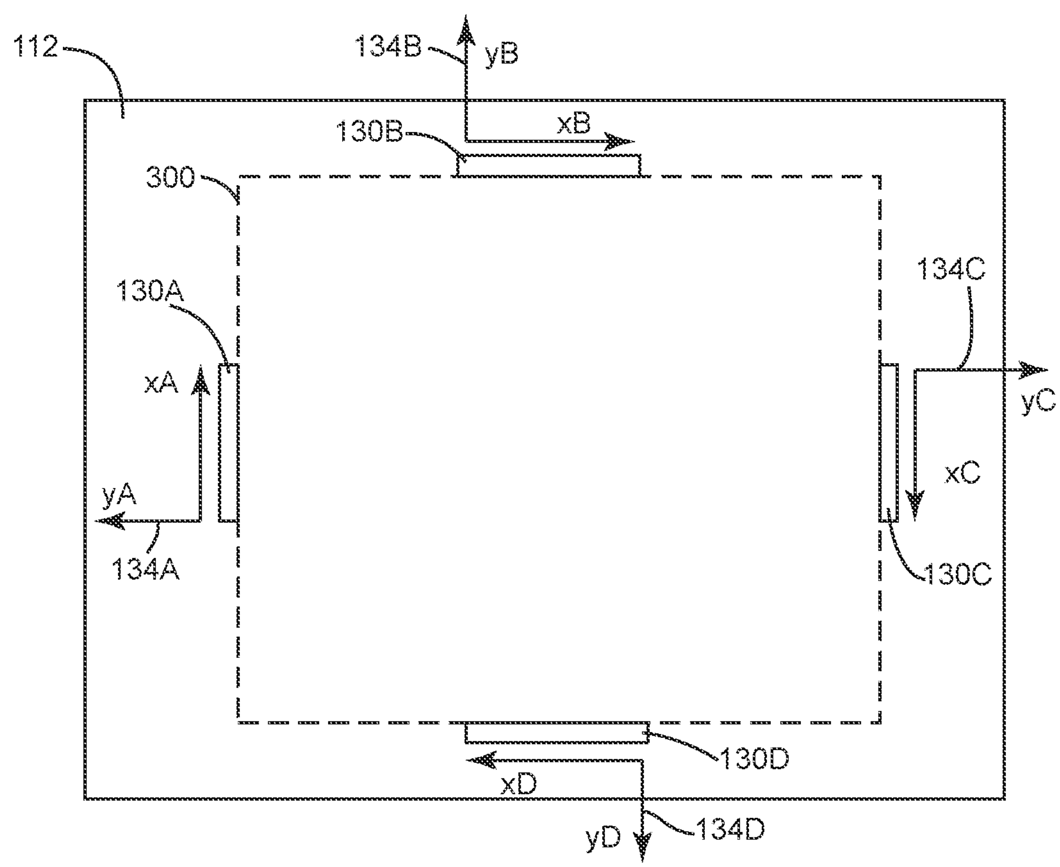
FIG. 4B illustrates a top view of the mounting system of FIG. 3 in the thermally neutral configuration.

FIG. 4A illustrates a side view of the mounting system 200 of FIG. 3 in a thermally neutral configuration. FIG. 4B illustrates a top view of the mounting system 200 of FIG. 3 in the thermally neutral configuration. In the thermally neutral configuration of FIGS. 4A-4B, the flexures 130A-130D are coupled to a mounted element 300 and unbent. If the mounted element 300 experiences thermal expansion or contraction with respect to the mounting system 200 and/or base due to a difference in the coefficients of thermal expansion of the materials of the mounted element 300, the mounting system 200 and/or the base, the mounting system may be in a thermally expansive or thermally contracted configuration.

Figure 5:
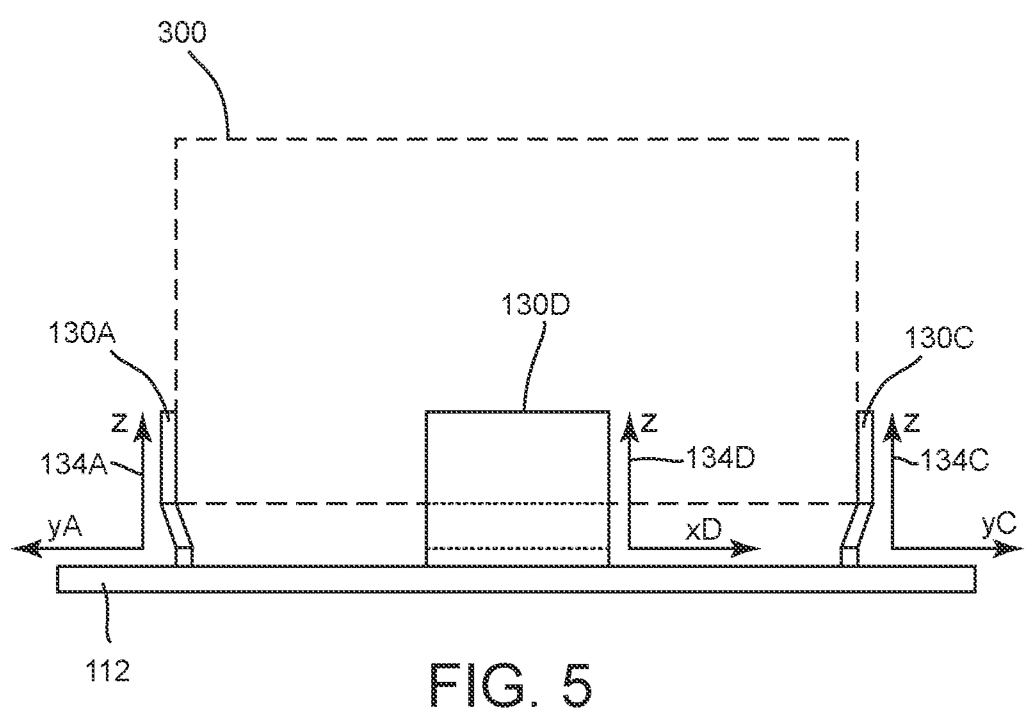
FIG. 5 illustrates a side view of the mounting system of FIG. 3 in a thermally expansive configuration.

FIG. 5 illustrates a side view of the mounting system 200 of FIG. 3 in a thermally expansive configuration. In the thermally expansive configuration, the flexures 130A-130D remain coupled to the mounted element 300, but are bent in an outward direction (along the respective y-axes defined by the flexures). Thus, the flexures 130A-130D act as leaf springs, each flexure providing flexibility in one direction (e.g. along the y-axis) and stiffness in an orthogonal direction (e.g., along the x-axis). As shown in FIG. 5, only a portion of the flexures 130A-130D may bend. In particular, a portion attached to the mounted element 300 and a portion proximal to the base 112 may maintain a fixed position.

Although the flexures 130A-130D bend outward, allowing the mounted element 300 to thermally expand, the flexures 130A-130D do not bend or deform in other directions (e.g., along the x-axis), maintaining alignment of the mounted element 300 with respect to the base. Additionally, each flexure 130A-130D may bend by an approximately equivalent amount and thus exert approximately the same force on the mounted element 300. Thus, the forces equalize, resulting in the mounted element 300 maintaining a fixed position relative to the base 112. In particular, the flexures 130A-130D may maintain an alignment of a center of an optical element (such as a beam splitter) to a center of a detector attached to the base 112. Moreover, there is very little, insignificant, movement along the Z-axis.

In an optical system with materials having different thermal coefficients of expansion, the bending of the flexures in one direction reduces stress on the components that would otherwise be present. However, the lack of bending or deformation of the flexures in other directions maintains the alignment of the system and, thus, provides stability to the system.

As shown, in embodiments, the mounting system 200 and its optics are not directly affixed to the detector. Instead, the mounting system 200 is affixed to the base (e.g., PCB), which in turn is affixed to the detector. This lack of direct connection between the mounting system and the detector in theory could cause the optics to fall out of alignment with respect to the detector. However, an unexpected result of the use of the flexures described in embodiments is that sub-micron alignment is maintained between the detector and optics in the mounting system 200 even without a direct attachment between the detector and the mounting system. In one embodiment, such alignment is facilitated by using a base that has a coefficient of thermal expansion that is approximately equal to a coefficient of thermal expansion of the detector.

The use of the flexures 130A-130D to attach the optical element 120 (or housing 122) to the base 112 rather than directly to the detector enables the detector to have a minimal package size. Thus, embodiments described herein facilitate miniaturization of devices for which precise optical alignment between components with possibly different coefficients of thermal expansion is important.

As noted above, although FIG. 3 shows four flexures 130A-130D, the mounting system 200 may include more or fewer flexures. FIGS. 6A-6D show embodiments of mounting systems having various numbers of flexures.

Figure 6A:
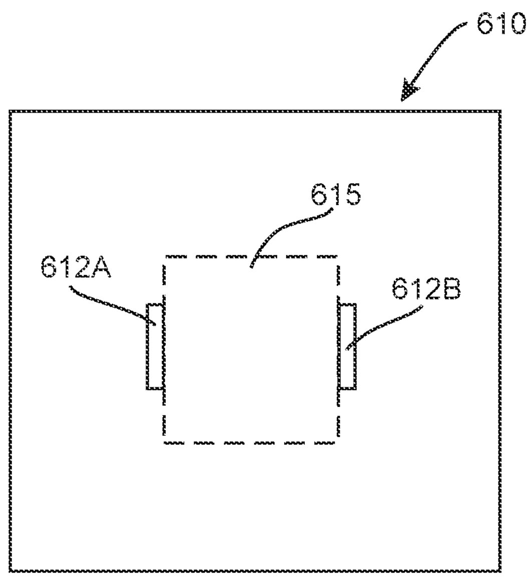
FIG. 6A illustrates a top view of an embodiment of a mounting system including two flexures according to one embodiment.

FIG. 6A illustrates a top view of an embodiment of a mounting system 610 including two flexures 612A-612B according to one embodiment. The flexures 612A-612B are disposed on opposite sides of a mounted element 615. Thus, in one embodiment, a mounting system may include a base having a substantially flat surface defining a base plane and two or more substantially flat flexures protruding from the base, the two or more substantially flat flexures respectively defining two or more flexure planes approximately perpendicular to the base plane, the two or more flexure planes respectively defining two or more flexure lines perpendicular to the flexure planes, wherein each of the two or more substantially flat flexures is flexible along a respective flexure line of the two or more flexure lines and is rigid perpendicular to the respective flexure line, and wherein the two or more flexure lines meet at an intersection point.

Similarly, an optical system may include a detector to determine one or more intensities of light impinging on one or more locations of the detector, an optical element to redirect light towards the detector along a detection axis, and two or more substantially flat flexures indirectly coupling the optical element to the detector, the two or more substantially flat flexures respectively defining two or more flexure planes parallel to the detection axis, each of the two or more substantially flat flexures being rigid along a respective first axis and flexible along a respective second axis, the respective first axis and the respective second axis being generally parallel to a face of the detector.

Figure 6B:
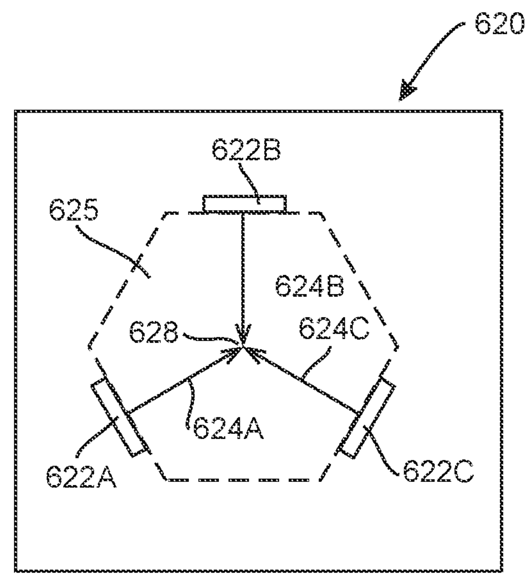
FIG. 6B illustrates a top view of an embodiment of a mounting system including three flexures according to one embodiment.

FIG. 6B illustrates a top view of an embodiment of a mounting system 620 including three flexures 622A-622C according to one embodiment. The flexures 622A-622C are disposed around a mounted element 625 such that flexure lines 624A-624C defined by the flexures 622A-622C meet at an intersection point 628 and form 120-degree angles with each other. Thus, the flexures 622A-622C are equally spaced about the mounted element 625. In other embodiments, the flexures 622A-622C are not equally spaced about the mounted element 625.

Figure 6C:
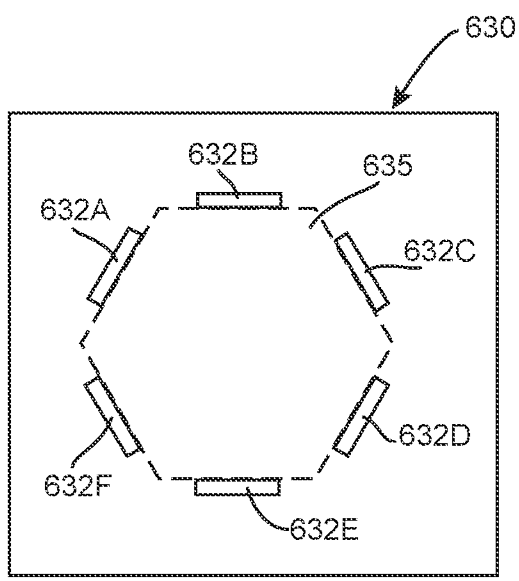
FIG. 6C illustrates a top view of an embodiment of a mounting system including six flexures according to one embodiment.
Figure 6D:
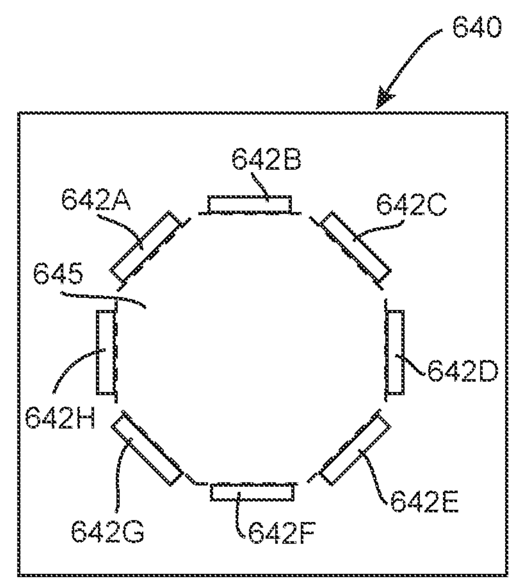
FIG. 6D illustrates a top view of an embodiment of a mounting system including eight flexures according to one embodiment.

FIG. 6C illustrates a top view of an embodiment of a mounting system 630 including six flexures 632A-632G according to one embodiment. Although the six flexures 632A-632F are shown disposed around the mounted element 635 with equal spacing, in other embodiments, the flexures 632A-632F may not be equally spaced about the mounted element 635. FIG. 6D illustrates a top view of an embodiment of a mounting system 640 including eight flexures 642A-642H according to one embodiment. Although the eight flexures 642A-642H are shown disposed around the mounted element 645 with equal spacing, in other embodiments, the flexures 642A-642H may not be equally spaced about the mounted element 645.

Figure 7:
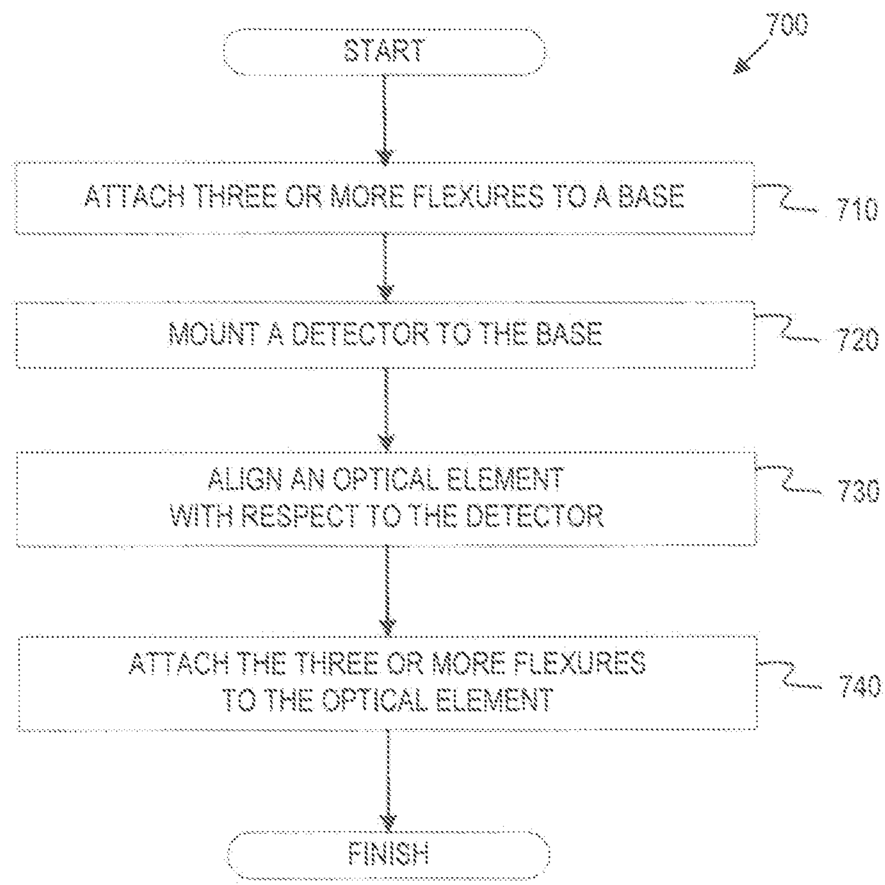
FIG. 7 is a flow chart showing a method of mounting an optical element.

FIG. 7 is a flow chart showing a method 700 of mounting an optical element. The method 700 begins in block 710 with attaching three or more flexures to a base. The base may include, for example, a printed circuit board (PCB). The flexures may be attached at a free end to the base such that the flexures protrude from the base. In one embodiment, the flexures are attached by welding or soldering the flexures to base. In another embodiment, the flexures may be glued to the base or otherwise attached.

In block 720, a detector is mounted to the base. The detector may be mounted to the base such that the detector contacts conductive tracings of the base to communicate data from the detector to a processor or other component. In one embodiment, the detector is glued or soldered to the base. The detector may be mounted to the base such that it is surrounded by, but does not contact, the flexures.

In block 730, an optical element is aligned with respect to the detector. The optical element may include, for example, a beam splitter. The optical element may be align in six degrees of freedom, e.g., three translational directions along a set of three perpendicular axes and three rotational directional about the axes. The optical element may be aligned with a sub-micron accuracy.

In block 740, the three or more flexures are attached to the optical element. In one embodiment, the three or more flexures are glued to the optical element (or a housing surrounding the optical element). In one embodiment, glue is applied to the flexures and the flexures are pressed against a portion of the optical element or the housing. In one embodiment, the flexures are glued to the optical element or the housing prior to alignment and the glue is cured after alignment has been performed. In another embodiment, the flexures are attached to the optical element in other ways.

It is to be understood that the above description is intended to be illustrative, and not restrictive. Many other embodiments will be apparent upon reading and understanding the above description. Although embodiments of the present invention have been described with reference to specific example embodiments, it will be recognized that the invention is not limited to the embodiments described, but can be practiced with modification and alteration within the spirit and scope of the appended claims. Accordingly, the specification and drawings are to be regarded in an illustrative sense rather than a restrictive sense. The scope of the invention should, therefore, be determined with reference to the appended claims, along with the full scope of equivalents to which such claims are entitled.

What is claimed is:

1. A scanner for scanning a dental site, the scanner comprising:

a base;

a detector mounted to the base;

a light source to generate light;

one or more optical elements to pass the light in a first direction to a dental site and to redirect returning light reflected off of the dental site towards the detector along a detection axis in a second direction; and a means for coupling the optical element to the base that maintains an alignment of the optical element to the detector with changes in temperature.

2. The scanner of claim 1, wherein the means for coupling the one or more optical elements to the base comprises two or more flexures.

3. The scanner of claim 1, wherein the means for coupling the one or more optical elements to the base maintains the alignment of the one or more optical elements to the detector during thermal expansion or contraction of the one or more optical elements with respect to at least one of the detector or the base.

4. The scanner of claim 1, wherein the one or more optical elements comprises a beam splitter.

5. The scanner of claim 4, wherein:

the one or more optical elements further comprises a microlens array to split the light into an array of light beams the beam splitter is to transmit the array of light beams towards the dental site and redirect a reflected array of light beams from the dental site towards the detector along the detection axis in the second direction; and the detector comprises one or more sensors, wherein each sensor of the one or more sensors is to determine an intensity of light impinging on the sensor.

6. The scanner of claim 1, wherein the light source comprises a semiconductor laser.

7. The scanner of claim 1, wherein the one or more optical elements comprises a polarizer to polarize the light.

8. The scanner of claim 1, wherein the one or more optical elements comprises confocal optics to perform confocal focusing of the light.

9. The scanner of claim 8, further comprising:

an actuator to change a relative focal plane of the confocal optics.

10. The scanner of claim 1, wherein the means for coupling the one or more optical elements to the base maintains an alignment of the one or more optical elements to the detector to a sub-micron level of accuracy and stability.

11. The scanner of claim 1, wherein the base comprises a printed circuit board (PCB) having a first coefficient of thermal expansion that is approximately equal to a second coefficient of thermal expansion of the detector, the one or more optical elements comprises an optical beam-splitting element in a housing, and the means for coupling the one or more optical elements to the base attaches the PCB to the housing.

12. The scanner of claim 11, wherein the housing comprises metal.

13. The scanner of claim 1, wherein the one or more optical elements have a first coefficient of thermal expansion that is different from a second coefficient of thermal expansion of at least one of the detector or the base.

14. A method comprising:

performing intraoral scanning, wherein performing the intraoral scanning comprises:

generating light by a light source of a scanner;

directing the light through one or more optical elements of the scanner, the one or more optical elements comprising a microlens array that splits the light into an array of light beams and a beam splitter that transmits the array of light beams towards a target;

redirecting, by the beam splitter, a reflected array of light beams from the target towards a detector, wherein the detector comprises a plurality of sensors; and determining, by each sensor of the plurality of sensors, a measurement of light impinging on the sensor; and maintaining an alignment of the one or more optical elements to the detector with changes in temperature during the intraoral scanning, wherein the maintained alignment of the one or more optical elements to the detector causes each reflected light beam of the array of light beams to be aligned with a respective sensor of the plurality of sensors.

15. The method of claim 14, wherein the changes in temperature cause thermal expansion or contraction of at least one of the one or more optical elements or a housing of the one or more optical elements with respect to at least one of the detector or a base on which the detector is mounted, and wherein the alignment of the one or more optical elements to the detector is maintained through the thermal expansion or contraction of at least one of the one or more optical elements or the housing of the one or more optical elements with respect to at least one of the detector or the base on which the detector is mounted.

16. The method of claim 14, wherein maintaining the alignment of the one or more optical elements to the detector with changes in temperature comprises:

responsive to a temperature change within the scanner that causes thermal expansion or contraction of at least one of the one or more optical elements or a housing of the one or more optical elements with respect to at least one of the detector or a base on which the detector is mounted, performing the following comprising:

flexing a first flexure in a first direction along a first flexure line that is defined by a first flexure plane of the first flexure, wherein the first flexure plane is approximately perpendicular to a base plane defined by the base, wherein the first flexure line is approximately perpendicular to the first flexure plane, and wherein the first flexure is rigid perpendicular to the first flexure line; and flexing a second flexure in a second direction along a second flexure line that is defined by a second flexure plane of the second flexure, wherein the second flexure plane is approximately perpendicular to the base plane, wherein the second flexure line is approximately perpendicular to the second flexure plane, and wherein the second flexure is rigid perpendicular to the second flexure line; and maintaining, by at least the first flexure and the second flexure, the alignment of the one or more optical elements to the detector.

17. The method of claim 16, wherein maintaining the alignment of the one or more optical elements to the detector with changes in temperature further comprises:

responsive to the temperature change within the scanner that causes thermal expansion or contraction of at least one of the one or more optical elements or the housing of the one or more optical elements with respect to at least one of the detector or the base on which the detector is mounted, flexing a third flexure in a third direction along a third flexure line that is defined by a third flexure plane of the third flexure, wherein the third flexure plane is approximately perpendicular to the base plane, wherein the third flexure line is approximately perpendicular to the third flexure plane, and wherein the third flexure is rigid perpendicular to the third flexure line;

wherein the alignment of the one or more optical elements to the detector is maintained by at least the first flexure, the second flexure and the third flexure.

18. The method of claim 14, further comprising:

performing confocal focusing of the array of light beams.

19. The method of claim 14, wherein at least one of a base on which the detector is mounted or the detector has a first coefficient of thermal expansion that is different from at least one of a second coefficient of thermal expansion of the one or more optical elements or a third coefficient of thermal expansion of a housing of the one or more optical elements.

20. The method of claim 14, wherein maintaining the alignment of the one or more optical elements to the detector comprises maintaining the alignment of the one or more optical elements to the detector to a sub-micron level of accuracy and stability.

* * * * *